(12) United States Patent  (10) Patent No.: US 7,604,403 B2
Yi  (45) Date of Patent: Oct. 20, 2009

(54) X-RAY IRRADIATING APPARATUS AND X-RAY IMAGING SYSTEM

(75) Inventor: Xiong Yi, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/331,949

(22) Filed: Dec. 10, 2008

(65) Prior Publication Data

US 2009/0154652 A1    Jun. 18, 2009

(51) Int. Cl.
  *H05G 1/06* (2006.01)
  *H05G 1/02* (2006.01)
(52) U.S. Cl. .................................. 378/194; 378/193
(58) Field of Classification Search .............. 378/119, 378/193–198
  See application file for complete search history.

(56) References Cited

U.S. PATENT DOCUMENTS

| 2,712,080 A | * | 6/1955 | Koerner ...................... 378/194 |
| 3,037,119 A | * | 5/1962 | Kizaur et al. ................. 378/194 |
| 3,118,066 A | | 1/1964 | Thomas et al. |
| 3,541,334 A | | 11/1970 | Sobolewski |
| 3,551,612 A | | 12/1970 | Guentner et al. |
| 3,891,856 A | * | 6/1975 | Amor et al. .................. 378/197 |
| 3,902,070 A | | 8/1975 | Amor, Jr. et al. |
| 4,001,593 A | * | 1/1977 | Wing et al. .................... 378/11 |
| 4,041,320 A | | 8/1977 | Amor, Jr. et al. |
| 4,063,104 A | * | 12/1977 | Gadd ........................... 378/11 |
| 4,114,043 A | | 9/1978 | Gansfried |
| 4,146,795 A | | 3/1979 | Braden et al. |
| 4,246,482 A | | 1/1981 | Zupancic |
| 4,343,996 A | | 8/1982 | Kuipers |
| 4,397,032 A | | 8/1983 | Kuipers |
| 4,435,830 A | | 3/1984 | Suzuki et al. |
| 4,501,011 A | | 2/1985 | Hauck et al. |
| 2008/0247516 A1 | | 10/2008 | Fink et al. |

FOREIGN PATENT DOCUMENTS

JP    11-155850    6/1999

* cited by examiner

*Primary Examiner*—Irakli Kiknadze
(74) *Attorney, Agent, or Firm*—Armstrong Teasdale LLP

(57) ABSTRACT

An X-ray irradiating apparatus includes an X-ray tube attached to a front end of a column suspended from a carriage, the carriage being displaceable along a rail parallel to a ceiling. The X-ray irradiating apparatus includes a power supply cable fixed at one end thereof to the carriage, a guide mechanism for guiding the cable along the rail upon displacement of the carriage, and a reaction force mechanism for applying to the carriage a reaction force which withstands a tension induced by slackening of the cable outside the guide mechanism.

20 Claims, 6 Drawing Sheets

X-RAY IRRADIATING APPARATUS AND X-RAY IMAGING SYSTEM

CROSS REFERENCE TO RELATED APPLICATIONS

This application claims the benefit of Chinese Patent Application No. 200710300943.6 filed Dec. 14, 2007, which is hereby incorporated by reference in its entirety.

BACKGROUND OF THE INVENTION

The embodiments described herein relate to an X-ray irradiating apparatus and an X-ray imaging system. Particularly, the embodiments described herein relate to an X-ray irradiating apparatus having an X-ray tube attached to a front end of a column suspended from a carriage displaceable along a rail parallel to a ceiling, as well as an X-ray imaging system.

In an X-ray imaging system, X-ray is radiated to a patient from an X-ray tube and transmitted X-ray is detected by an X-ray detector. According to one type of an X-ray imaging system it is used an X-ray tube attached to a front end of a column suspended from a carriage that is displaceable along a rail parallel to a ceiling. In such a type of an X-ray imaging system, the position of the carriage, extension and contraction of the column and the direction of the X-ray tube are adjusted in accordance with the purpose of radiographing (see, for example, Japanese Unexamined Patent Publication No. Hei 11(1999)-155850).

A cable for the supply of electric power to the X-ray tube is connected to the carriage. Since the cable is thick and heavy, a large force is needed for displacing the carriage manually. Thus, the working efficiency for carriage displacement is poor.

It is desirable that the problem described previously is solved.

BRIEF DESCRIPTION OF THE INVENTION

In a first aspect of the invention there is provided an X-ray irradiating apparatus including an X-ray tube attached to a front end of a column suspended from a carriage, the carriage being displaceable along a rail parallel to a ceiling, a power supply cable fixed at one end thereof to the carriage, a guide mechanism for guiding the cable along the rail upon displacement of the carriage, and a reaction force mechanism for applying to the carriage a reaction force which withstands a tension induced by slackening of the cable outside the guide mechanism.

In a second aspect of the invention there is provided, in combination with the above first aspect, an X-ray irradiating apparatus wherein the reaction force mechanism includes a belt entrained around a pulley and extending in parallel with the rail, a connecting member for connecting the carriage to the belt, and a spring for applying the reaction force to the belt.

In a third aspect of the invention there is provided, in combination with the above second aspect, an X-ray irradiating apparatus wherein the reaction force of the spring increases with displacement of the carriage in a slack increasing direction and decreases with displacement of the carriage in a slack decreasing direction of the cable.

In a fourth aspect of the invention there is provided, in combination with the above third aspect, an X-ray irradiating apparatus wherein the spring is a spiral spring.

In a fifth aspect of the invention there is provided, in combination with the above fourth aspect, an X-ray irradiating apparatus wherein the spiral spring applies the reaction force to the belt through the pulley.

In a sixth aspect of the invention there is provided, in combination with the above fifth aspect, an X-ray irradiating apparatus wherein the pulley is mounted to a fixed shaft rotatably, and the spiral spring is connected at one end thereof to the fixed shaft and at an opposite end thereof to the pulley.

In a seventh aspect of the invention there is provided in combination with the above sixth aspect, an X-ray irradiating apparatus wherein the pulley has a coaxial hollow portion, and within the hollow portion the spiral spring is connected at an inner end thereof to the fixed shaft and at an outer end thereof to an inner wall of the hollow portion.

In an eighth aspect of the invention there is provided, in combination with the above second aspect, an X-ray irradiating apparatus wherein the belt is a toothed belt and the pulley is a toothed pulley.

In a ninth aspect of the invention there is provided, in combination with the above first aspect, an X-ray irradiating apparatus wherein the guide mechanism has a plurality of rollers disposed along the rail.

In a tenth aspect of the invention there is provided, in combination with the above ninth aspect, an X-ray irradiating apparatus wherein the plural rollers are disposed on the same side as the belt with respect to the rail.

In an eleventh aspect of the invention there is provided an X-ray imaging system including: an X-ray tube attached to a front end of a column suspended from a carriage, the carriage being displaceable along a rail parallel to a ceiling; an X-ray detector opposed to the X-ray tube; a power supply cable fixed at one end thereof to the carriage; a guide mechanism for guiding the cable along the rail upon displacement of the carriage; and a reaction force mechanism for applying to the carriage a reaction force which withstands a tension induced by slackening of the cable outside the guide mechanism.

In a twelfth aspect of the invention there is provided, in combination with the above eleventh aspect, an x-ray imaging system wherein the reaction force mechanism includes a belt entrained around a pulley and extending in parallel with the rail, a connecting member for connecting the carriage to the belt, and a spring for applying the reaction force to the belt.

In a thirteenth aspect of the invention there is provided, in combination with the above twelfth aspect, an X-ray imaging system wherein the reaction force of the spring increases with displacement of the carriage in a slack increase direction of the cable and decreases with displacement of the carriage in a slack decreasing direction of the cable.

In a fourteenth aspect of the invention there is provided in combination with the above thirteenth aspect, an X-ray imaging system wherein the spring is a spiral spring.

In a fifteenth aspect of the invention there is provided, in combination with the fourteenth aspect, an X-ray imaging system wherein the spiral spring applies the reaction force to the belt through the pulley.

In a sixteenth aspect of the invention there is provided in combination with the fifteenth aspect, an X-ray imaging system wherein the pulley is mounted to a fixed shaft rotatably and the spiral spring is connected at one end thereof to the fixed shaft and at an opposite end thereof to the pulley.

In a seventeenth aspect of the invention there is provided, in combination with the above sixteenth aspect, an X-ray imaging system wherein the pulley has a coaxial hollow portion, and within the hollow portion the spiral spring is connected an inner end thereof to the fixed shaft and at an outer end thereof to an inner wall of the hollow portion.

In an eighteenth aspect of the invention there is provided, in combination with the above twelfth aspect, an X-ray imaging system wherein the belt is a toothed belt and the pulley is a toothed pulley.

In a nineteenth aspect of the invention there is provided in combination with the above eleventh aspect, an X-ray imaging system wherein the guide mechanism has a plurality of rollers disposed along the rail.

In a twentieth aspect of the invention there is provided, in combination with the above nineteenth aspect, an X-ray imaging system wherein the plural rollers are disposed on the same side as the belt with respect to the rail.

In the above first aspect of the invention, since the X-ray irradiating apparatus including an X-ray tube attached to a front end of a column suspended from a carriage, the carriage being displaceable along a rail parallel to a ceiling, further includes a power supply cable fixed at one end thereof to the carriage, a guide mechanism for guiding the cable along the rail upon displacement of the carriage, and a reaction force mechanism for applying to the carriage a reaction force which withstands a tension induced by slackening of the cable outside the guide mechanism, the X-ray irradiating apparatus is superior in the working efficiency for carriage displacement.

In the above eleventh aspect of the invention, since the X-ray imaging system including an X-ray tube attached to a front end of a column suspended from a carriage, the carriage being displaceable along a rail parallel to a ceiling, and an X-ray detector opposed to the X-ray tube, further includes a power supply cable fixed at one end thereof to the carriage, a guide mechanism for guiding the cable along the rail upon displacement of the carriage, and a reaction force mechanism for applying to the carriage a reaction force which withstands a tension induced by slackening of the cable outside the guide mechanism, the X-ray imaging system is superior in the working efficiency for carriage displacement.

In the above second and twelfth aspects of the invention, since the reaction force mechanism includes a belt entrained around a pulley and extending in parallel with the rail, a connecting member for connecting the carriage to the belt, and a spring for applying the reaction force to the belt, it is possible to let the reaction force act on the carriage in an appropriate manner.

In the above third or thirteenth aspect of the invention, since the reaction force of the spring increases with displacement of the carriage in a slack increasing direction of the cable and decreases with displacement of the carriage in a slack decreasing direction of the cable, it is possible to obtain a reaction force matching a change in tension of the cable.

In the above fourth or fourteenth aspect of the invention, since the spring is a spiral spring, it is possible to effect space saving.

In the above fifth or fifteenth aspect of the invention, since the spiral spring applies the reaction force to the belt through the pulley, it is possible to let the reaction force act on the belt in an appropriate manner.

In the above sixth or sixteenth aspect of the invention, since the pulley is mounted to a fixed shaft rotatably and the spiral spring is connected at one end thereof to the fixed shat and at an opposite end to the pulley, it is possible to let the reaction force act on the pulley in an appropriate manner.

In the above seventh or seventeenth aspect of the invention, since the pulley has a coaxial hollow portion, and within the hollow portion the spiral spring is connected at an inner end thereof to the fixed shaft and at an outer end thereof to an inner wall of the hollow portion, it is possible to effect space saving.

In the above eighth or eighteenth aspect of the invention, since the belt is a toothed belt and the pulley is a toothed pulley, it is possible to effect a positive transfer of the reaction force.

In the above ninth or nineteenth aspect of the invention, since the guide mechanism has a plurality of rollers disposed along the rail, it is possible to guide the cable smoothly.

In the above tenth or twentieth aspect of the invention, since the plural rollers are disposed on the same side as the belt with respect to the rail, it is possible to improve the working efficiency for set-up and maintenance.

Further objects and advantages of the present invention will be apparent from the following description of the preferred embodiments of the invention as illustrated in the accompanying drawings.

DETAILED DESCRIPTION OF THE INVENTION

Embodiments of the invention will be described below with reference to the drawings, however the invention is not limited to the embodiments described herein.

Figure 1:
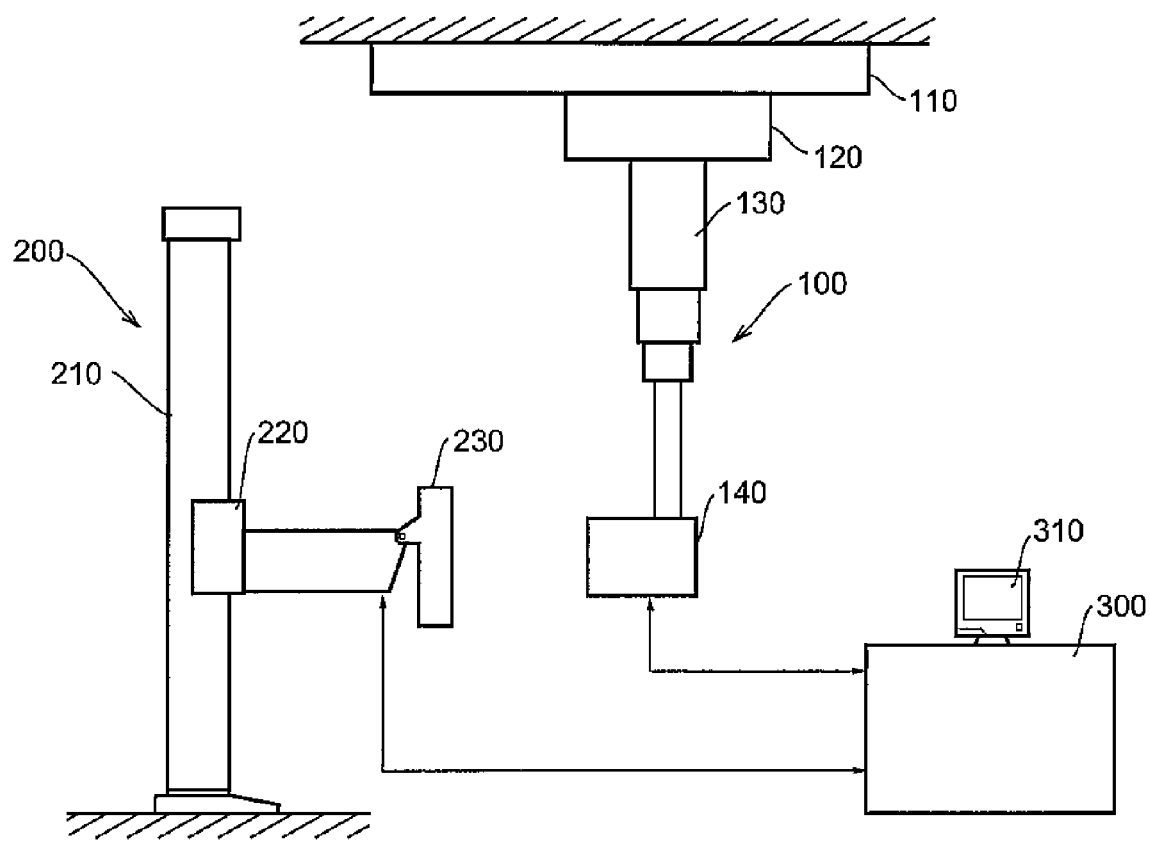
FIG. 1 illustrates the construction of an X-ray imaging system as an example of the best mode for carrying out the invention.

FIG. 1 schematically shows the construction of an exemplary X-ray imaging system.

As shown in FIG. 1, the X-ray imaging system has an X-ray irradiating apparatus 100. The X-ray irradiating apparatus 100 is one example of an X-ray irradiating apparatus that may be used with the X-ray imaging system shown in FIG. 1.

According to the construction of the X-ray irradiating apparatus 100, an X-ray tube 140 is attached to a front end of column 130 suspended from a carriage 120, the carriage 120 being displaceable along a rail 110 laid on a ceiling. The X-ray tube 140 can change its direction so that the X-ray irradiating direction can be changed. The column 130 that supports the X-ray tube 140 is capable of expansion and contraction in the longitudinal direction. Such a construction is also called OTS (overhead tube suspension).

The rail 110 is an example of the rail defined in the invention. The carriage 120 is an example of the carriage defined in the invention. The column 130 is an example of the column defined in the invention. The X-ray tube 140 is an example of the X-ray tube defined in the invention.

The X-ray imaging system also has an X-ray detecting apparatus 200. According to the construction of the X-ray detecting apparatus 200, a column 210 is erected vertically on a floor, a carriage 220 is attached to the column 210 so as to be movable vertically, and an X-ray detector 230 is attached to a front end of an arm of the carriage 220.

The X-ray detector 230 is a flat plate-like structure and has an X-ray incidence surface whose direction can be changed in accordance with an X-ray incidence direction. The X-ray detector 230 contains a two-dimensional array of X-ray detecting elements. The X-ray detector 230 is an example of the X-ray detector defined in the invention.

A detection signal provided from the X-ray detector 230 is inputted to an operator console 300. On the basis of the input signal provided from the X-ray detector 230 the operator console 300 reconstructs a radioscopic image of an object to be radiographed. The radioscopic image is displayed on a display 310.

The X-ray detector 230 may be one that holds an X-ray film cassette instead of the two-dimensional array of X-ray detecting elements. In case of using the X-ray film cassette, the radioscopic image is visualized by development.

Under operation performed by an operator the operator console 300 controls both X-ray irradiating apparatus 100 and X-ray detecting apparatus 200. For the X-ray irradiating apparatus 100 the operator console 300 controls X-ray intensity and irradiation timing. For the X-ray detecting apparatus 200 the operator console 300 controls the height of the X-ray detector 230 to match the height of the X-ray tube 140 and also controls the direction of the X-ray incidence surface of the X-ray detector 230 in conformity with the X-ray incidence direction.

Figure 2:
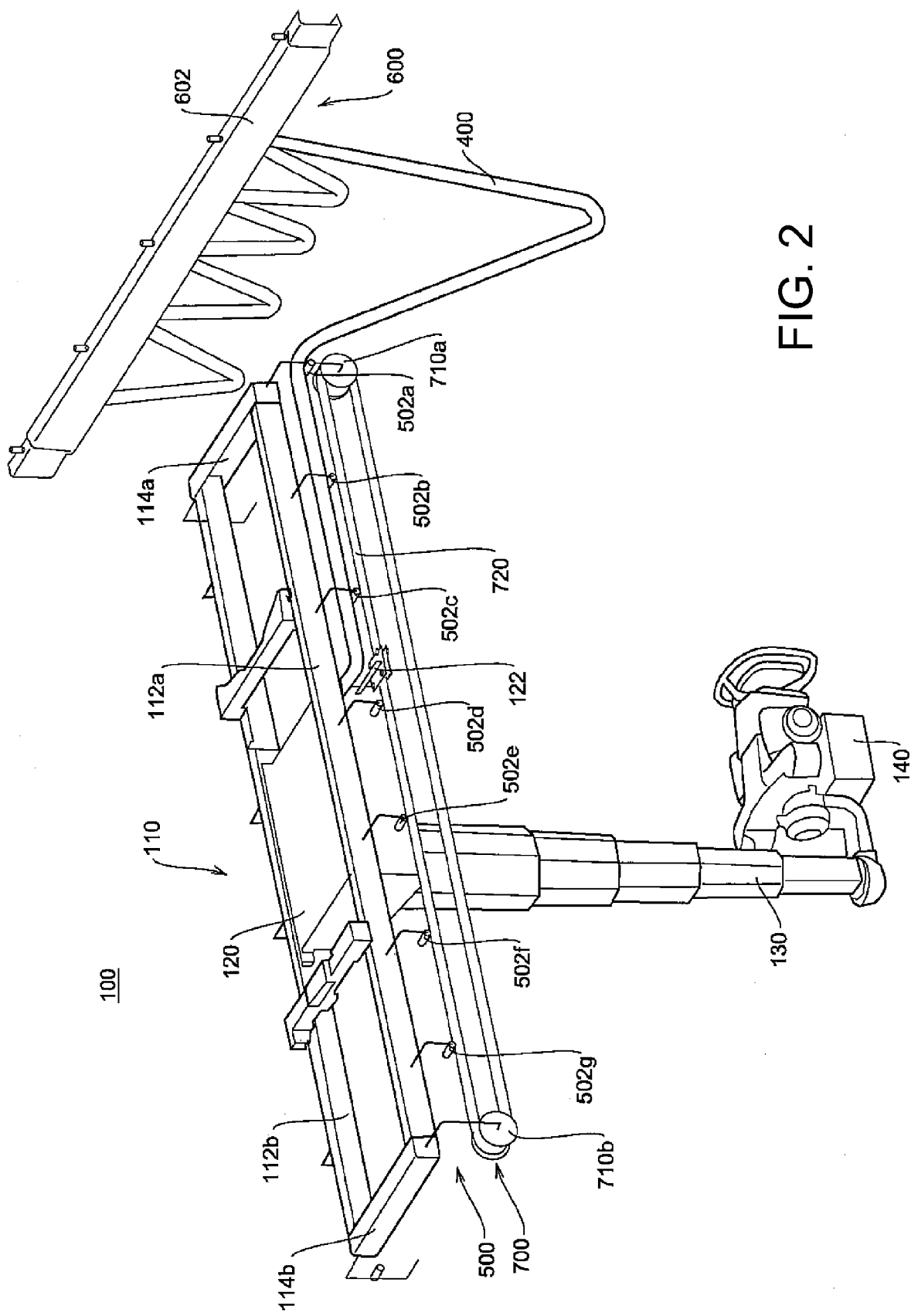
FIG. 2 illustrates the construction of an X-ray irradiating apparatus as another example of the best mode for carrying out the invention.

FIG. 2 shows the construction of the X-ray irradiating apparatus 100 in more detail. As shown in the same figure, the rail 110 has a pair of parallel rail members 112a and 112b. The rail members 112a and 112b are connected with each other at respective both ends by a pair of cross beam members 114a and 114b. With these components, the rail 110 is constituted as a rectangular frame structure. This rectangular frame structure will hereinafter be referred to as the "bridge."

The bridge 110 is movable in parallel in a direction perpendicular to the rail members 112a and 112b and along a rail (not shown) installed on the ceiling. When such a parallel movement is not needed, the bridge 110 may be fixed to the ceiling.

The carriage 120 engages the rail members 112a and 112b through rollers or sliders mounted on both sides of the carriage and can displace itself along the rail members 112a and 112b. By combining such a displacement with the parallel movement of the bridge 110 the carriage 120 can be displaced two-dimensionally along the ceiling.

One end of a cable 400 that is for the supply of electric power to the X-ray tube 140 is connected to one side of the carriage 120. The cable 400 is an example of the cable defined in the invention. In the vicinity of the rail member 112a the cable 400 is supported by a cable guide 500.

The cable guide 500 has plural rollers 502a to 502g disposed along the rail member 112a. The axes of the rollers 502a to 502g are horizontal and perpendicular to the rail member 112a.

The cable 400 is guided along the rail member 112a by the rollers 502a to 502g, whereby the cable 400 is guided smoothly without sagging halfway of the bridge 120. The cable guide 500 is an example of the guide mechanism defined in the invention. The rollers 502a to 502g are an example of the roller defined in the invention.

The cable 400 once slacks just after leaving the cable guide 500 and is then connected to a power supply (not shown) via a cable suspending mechanism 600. The cable suspending mechanism 600 suspends the cable 400 at several intermediate positions along a rail 602 with use of plural hooks or the like.

The rail 602 extends in the parallel movement direction of the bridge 110 and the plural hooks or the like are movable along the rail 602. Consequently, the slack portion of the cable 400 just after leaving the cable guide 500 becomes movable in parallel, following the parallel movement of the bridge 110. The slack portion of the cable 400 just after leaving the cable guide 500 will hereinafter be referred to simply as slack of the cable 400.

The amount of slack of the cable 400 changes according to the position of the carriage 120 on the bridge 110. It becomes larger as the carriage moves closer to the cable suspending mechanism 600 and it becomes smaller as the carriage 120 moves away from the cable suspending mechanism 600. The direction in which the carriage 120 moves closer to the cable suspending mechanism 600 will hereinafter be referred to as the right-hand direction, while the direction in which the carriage moves away from the cable suspending mechanism will hereinafter be referred to as the left-hand direction.

A tension based on the weight of slack of the cable 400 is imposed on the cable. The direction of the tension is the right-hand direction with respect to the cable 400 on the cable guide 500. The larger the amount of slack, the higher the tension, while the smaller the amount of slack, the lower the tension.

The tension in question acts as an assisting force for a displacement in the right-hand direction of the carriage 120, while it acts as a resisting force against a displacement in the left-hand direction of the carriage. Both such assisting force and resisting force vary according to the position of the carriage 120 on the bridge 110. They become larger as the carriage 120 moves rightward of the bridge 110, while they become smaller as the carriage moves leftwards of the bridge.

A reaction force mechanism 700 is provided to cancel such assisting force and resisting force. The reaction force mechanism 700 has two pulleys 710a, 710b and a belt 720. The belt 720 is entrained around the pulleys 710a and 710b in an endless manner.

The reaction force mechanism 700 is an example of the reaction force mechanism defined in the invention. The pulleys 710a and 710b are an example of the pulley defined in the invention. The belt 720 is an example of the belt defined in the invention.

The pulleys 710a and 710b are mounted at both ends respectively of the bridge 110 so as to be positioned below the cable guide 500. The axes of the pulleys 710a and 710b are parallel to the axes of the rollers 502a to 502g. Thus, the belt 720 extends below the cable guide 500 and along the bridge 110 and cable guide 500.

Toothed pulleys are used as the pulleys 710a and 710b, while a toothed belt is used as the belt 720. The toothed pulleys are also called gears, while the toothed belt is also called a timing belt. The pulleys 710a, 710b and the belt 720 need not be toothed when the frictional force between them is sufficiently large.

The pulley 710a located on the right-hand side is a drum pulley and is internally provided with a spiral spring for generation of a reaction force. Thus, the pulley 710a is a reaction force generating pulley. The pulley 710b located on the left-hand side may be used as a reaction force generating pulley, or both pulleys 710a and 710b may be used as reaction force generating pulleys. The following description refers to an example in which the right-hand pulley 710a is a reaction force generating pulley, but the following description also applies to the case where the left-hand or both pulleys are reaction force generating pulleys.

A front end portion of a lateral arm 122 extending from a side face of the carriage 120 is connected to an upper travel portion of the belt 720. The lateral arm 122 extends toward the belt 720 from under the connection of the cable 400 to the carriage 120. The lateral arm 122 is an example of the connecting member defined in the invention. Through such a connection the reaction force generated in the pulley 710a is transmitted to the carriage 120 through the belt 720.

Figure 3:
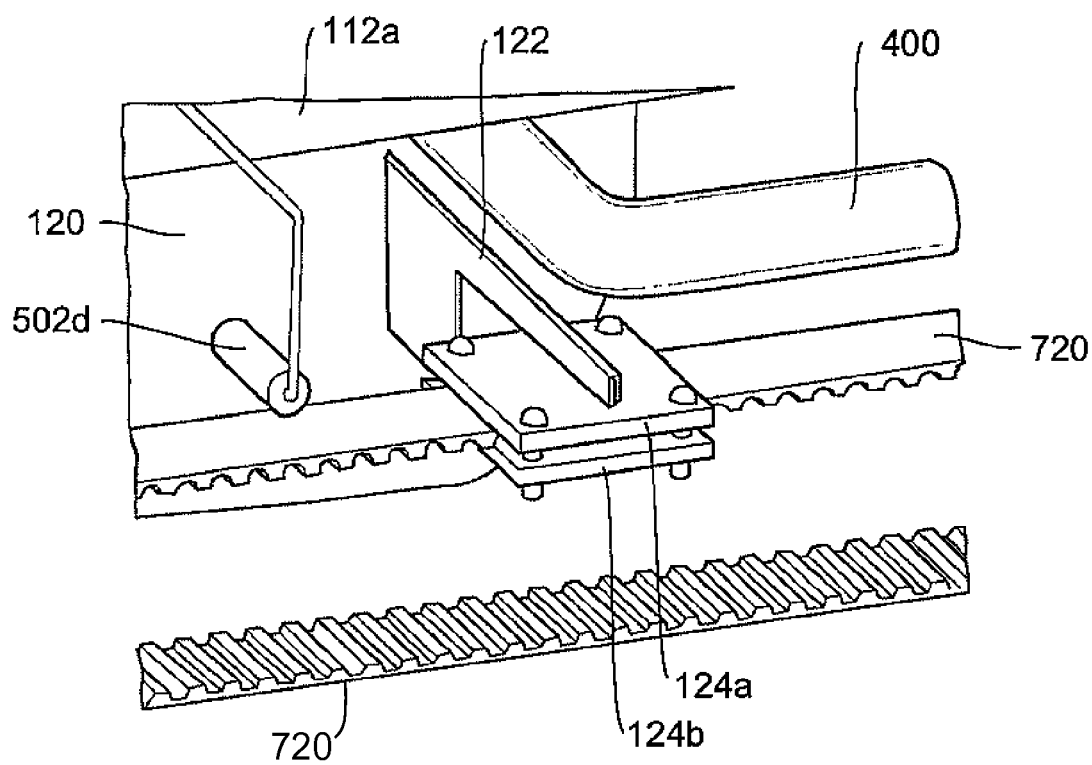
FIG. 3 illustrates a state of connection between a lateral arm and a belt.

FIG. 3 shows a state of connection between the lateral arm 122 and the belt 720. As shown in the same figure, the lateral arm 122 has two mounting plates 124a and 124b that constitute front end portions. The belt 720 is vertically held grippingly by the mounting plates 124a and 124b.

Figure 4:
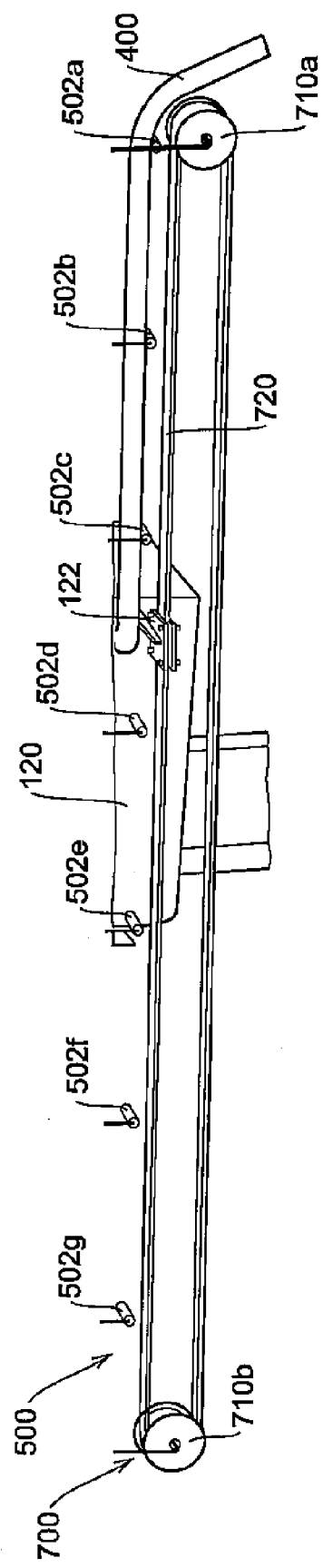
FIG. 4 illustrates a correlation among carriage, cable, cable guide and reaction force mechanism.

FIG. 4 shows a correlation among the carriage 120, cable 400, cable guide 500 and reaction force mechanism 700. As shown in the same figure, the cable 400 connected at one end thereof to a side face of the carriage 120 is guided by the cable guide 500 and the front end portion of the lateral arm 122 of the carriage 120 is connected to the upper travel portion of the belt 720 extending along the cable guide 500.

Figure 5:
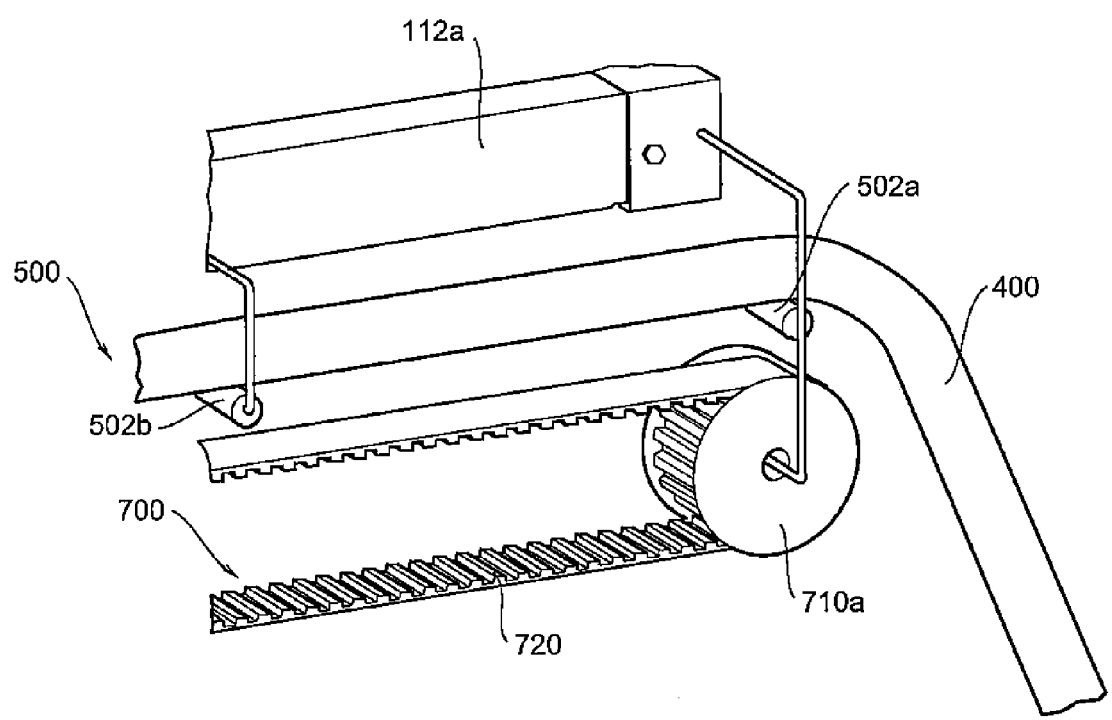
FIG. 5 illustrates a correlation among cable, cable guide, pulley and belt.

FIG. 5 shows a relation among the cable 400, cable guide 500, pulley 710a and belt 720 in the vicinity of the right end of the reaction force mechanism 700. As shown in the same figure, the cable 400 is guided by the rollers 502a and 502b of the cable guide 500 and sags just after leaving the roller 502a rightwards. The axis of the roller 502a and that of the pulley 710a are parallel to each other and the belt 720 is entrained around the pulley 710a.

Figure 6:
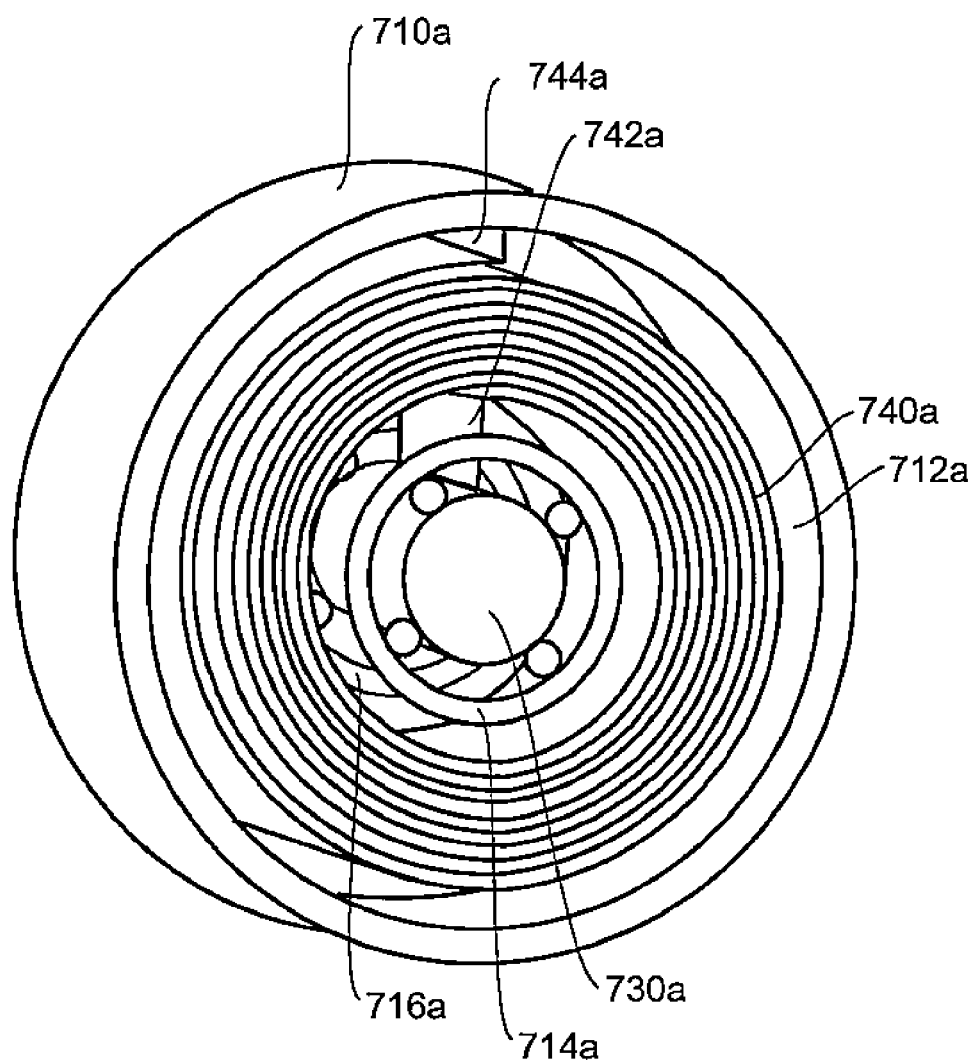
FIG. 6 illustrates an internal structure of a pulley.

FIG. 6 shows an internal structure of the pulley 710a. As shown in the same figure, the pulley 710a is a drum type pulley and is internally provided with a coaxial hollow portion 712a. The hollow portion 712a is an example of the hollow portion defined in the invention. The pulley 710a is mounted on a fixed central shaft 730a rotatably by hubs 714a, 716a and through bearings respectively. The central shaft 730a is an example of the fixed shaft defined in the invention.

A spiral spring 740a is accommodated within the hollow portion 712a of the pulley 710a. An inner end 742a of the spiral spring 740a is fixed to the central shaft 730a, while an outer end 744a thereof is fixed to an inner wall of the hollow portion 712a. The spiral spring 740a is wound up with clockwise rotation of the pulley 710a. The spiral spring 740a is an example of the spring defined in the invention and is also an example of the spiral spring defined in the invention.

The spiral spring 740a is in a natural state when the carriage 120 lies at the left end of the bridge 110. Alternatively, the spiral spring 740a may be in a moderately wound-up state to match tension of the cable 400.

If the carriage 120 is displaced toward the right end of the bridge from this state, a right-hand displacement of the upper travel portion of the belt 720 causes a clockwise rotation of the pulley 710a and the spiral spring 740a is wound up. The reaction force of the spiral spring 740a increases as the wound-up quantity of the spiral spring increases, and it reaches its maximum when the carriage 120 arrives at the right end of the bridge 110.

If the carriage 120 is displaced toward the left end of the bridge from this state, a left-hand displacement of the upper travel portion of the belt 720 causes a counterclockwise rotation of the pulley 710a and the spiral spring 740a is unwound. The reaction force of the spiral spring 740a decreases as the unwound quantity of the spiral spring increases, and it reaches its minimum when the carriage 120 arrives at the left end of the bridge 110.

A spring constant of the spiral spring 740a is selected so that such a change of the reaction force becomes balanced with a change in tension of the cable 400 induced by the displacement of the carriage 120. Therefore, the displacement of the carriage 120 can be done always with a constant force irrespectively of the change in tension of the cable 400.

Consequently, a manual operability for displacement of the carriage 120 is greatly improved. Moreover, even when the displacement of the carriage 120 is performed using the power of a motor or the like, a constant driving force is ensured and therefore the controllability is improved.

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray irradiating apparatus comprising:
    a carriage configured to move along a rail oriented parallel to a ceiling;
    an X-ray tube coupled to a front end of a column suspended from said carriage;
    a power supply cable coupled at a first end to said carriage;
    a guide mechanism configured to guide said cable along said rail upon movement of said carriage; and
    a reaction force mechanism configured to apply a reaction force to said carriage which withstands a tension induced by slackening of said cable outside said guide mechanism.

2. An X-ray irradiating apparatus according to claim 1, wherein said reaction force mechanism comprises:
    a belt entrained around a pulley and extending in parallel with said rail;
    a connecting member configured to couple said carriage to said belt; and
    a spring configured to apply the reaction force to said belt.

3. An X-ray irradiating apparatus according to claim 2, wherein the reaction force applied by said spring increases with movement of said carriage in a slack increasing direction of said cable and decreases with movement of said carriage in a slack decreasing direction of said cable.

4. An X-ray irradiating apparatus according to claim 3, wherein said spring comprises a spiral spring.

5. An X-ray irradiating apparatus according to claim 4, wherein said spiral spring is configured to apply the reaction force to said belt through said pulley.

6. An X-ray irradiating apparatus according to claim 5, wherein said pulley is rotatably coupled to a fixed shaft, and said spiral spring is coupled at a first end to said fixed shaft and at a second end to said pulley.

7. An X-ray irradiating apparatus according to claim 6, wherein said pulley comprises a coaxial hollow portion, said spiral spring is coupled at said first end to said fixed shaft and at said second end to an inner wall of said hollow portion.

8. An X-ray irradiating apparatus according to claim 2, wherein said belt comprises a toothed belt and said pulley comprises a toothed pulley.

9. An X-ray irradiating apparatus according to claim 1, wherein said guide mechanism comprises a plurality of rollers disposed along said rail.

10. An X-ray irradiating apparatus according to claim 9, wherein said plurality of rollers are disposed on a same side as said belt with respect to said rail.

11. An X-ray imaging system comprising:
    a carriage configured to move along a rail oriented parallel to a ceiling;
    an X-ray tube coupled to a front end of a column suspended from said carriage;
    a power supply cable coupled at a first end to said carriage;
    a guide mechanism configured to guide said cable along said rail upon movement of said carriage;
    a reaction force mechanism configured to apply a reaction force to said carriage which withstands a tension induced by slackening of said cable outside said guide mechanism;

an X-ray detector configured to detect X-rays emitted by said X-ray tube; and an operator console configured to reconstruct an image based on the X-rays detected by said X-ray detector.

12. An X-ray imaging system according to claim 11, wherein said reaction force mechanism comprises:
   a belt entrained around a pulley and extending in parallel with said rail;
   a connecting member configured to couple said carriage to said belt; and
   a spring configured to apply the reaction force to said belt.

13. An X-ray imaging system according to claim 12, wherein the reaction force applied by said spring increases with movement of said carriage in a slack increasing direction of said cable and decreases with movement of said carriage in a slack decreasing direction of said cable.

14. An X-ray imaging system according to claim 13, wherein said spring comprises a spiral spring.

15. An X-ray imaging system according to claim 14, wherein said spiral spring is configured to apply the reaction force to said belt through said pulley.

16. An X-ray imaging system according to claim 15, wherein said pulley is rotatably coupled to a fixed shaft, and said spiral spring is coupled at a first end to said fixed shaft and at a second end to said pulley.

17. An X-ray imaging system according to claim 16, wherein said pulley comprises a coaxial hollow portion, said spiral spring is coupled at said first end to said fixed shaft and at said second end to an inner wall of said hollow portion.

18. An X-ray imaging system according to claim 12, wherein said belt comprises a toothed belt and said pulley comprises a toothed pulley.

19. An X-ray imaging system according to claim 11, wherein said guide mechanism comprises a plurality of rollers disposed along said rail.

20. An X-ray imaging system according to claim 19, wherein said plurality of rollers are disposed on a same side as said belt with respect to said rail.

* * * * *